United States Patent
Sano

(10) Patent No.: US 8,006,560 B2
(45) Date of Patent: Aug. 30, 2011

(54) LASER ULTRASONIC PROPERTY MEASUREMENT APPARATUS

(75) Inventor: Mitsuhiko Sano, Minato-ku (JP)

(73) Assignee: Toshiba Mitsubishi-Electric Industrial Systems Corporation, Tokyo (JP)

( * ) Notice: Subject to any disclaimer, the term of this patent is extended or adjusted under 35 U.S.C. 154(b) by 312 days.

(21) Appl. No.: 12/297,103

(22) PCT Filed: Apr. 14, 2006

(86) PCT No.: PCT/JP2006/307941
§ 371 (c)(1),
(2), (4) Date: Nov. 12, 2008

(87) PCT Pub. No.: WO2007/122688
PCT Pub. Date: Nov. 1, 2007

(65) Prior Publication Data
US 2009/0090187 A1   Apr. 9, 2009

(51) Int. Cl.
*G01N 29/34*  (2006.01)
*G01N 29/06*  (2006.01)

(52) U.S. Cl. .......................................... 73/643
(58) Field of Classification Search ............... 73/643
See application file for complete search history.

(56) References Cited

U.S. PATENT DOCUMENTS

| | | | | |
|---|---|---|---|---|
| 4,028,932 A | * | 6/1977 | Rosencwaig | ............ 73/579 |
| 4,512,197 A | * | 4/1985 | von Gutfeld et al. | ............ 73/643 |
| 5,153,677 A | | 10/1992 | Keck et al. | |
| 5,718,231 A | | 2/1998 | Dewhurst et al. | |
| 5,748,564 A | | 5/1998 | Pattanayak | |
| 6,069,703 A | * | 5/2000 | Banet et al. | ............ 356/432 |
| 6,477,898 B1 | * | 11/2002 | Han et al. | ............ 73/579 |
| 2002/0026833 A1 | * | 3/2002 | Autrey et al. | ............ 73/643 |
| 2004/0040379 A1 | * | 3/2004 | O'Donnell et al. | ............ 73/627 |

FOREIGN PATENT DOCUMENTS

| | | |
|---|---|---|
| EP | 0 614 084 B1 | 5/1997 |
| JP | 7 248294 | 9/1995 |
| JP | 10 503028 | 3/1998 |
| JP | 2001 56298 | 2/2001 |
| JP | 2003 279501 | 10/2003 |
| JP | 2004 101189 | 4/2004 |
| JP | 2004 333275 | 11/2004 |
| JP | 2004 340759 | 12/2004 |
| JP | 3644611 | 2/2005 |
| JP | 2005 164488 | 6/2005 |
| TW | 332348 | 5/1998 |
| TW | 591689 | 6/2004 |
| TW | 1233763 | 6/2005 |

* cited by examiner

OTHER PUBLICATIONS

Office Action Issued Jan. 31, 2011, in Chinese Patent Application No. 200680054612.2 with English traslation.

*Primary Examiner* — Hezron Williams
*Assistant Examiner* — Rose M Miller
(74) *Attorney, Agent, or Firm* — Oblon, Spivak, McClelland, Maier & Neustadt, L.L.P.

(57) ABSTRACT

A mode of the present invention includes a transmitter (12) for shooting exciting laser light to an object of measurement (M) to excite ultrasonic waves in the object of measurement (M), a receiver (14) for shooting probing laser light to the object of measurement (M) to receive reflected light of probing laser light from the object of measurement (M) for detection of ultrasonic waves, a light blocking structure (16) having a first opening (16*a*) allowing the object of measurement (M) to pass therethrough and operable to accommodate the object of measurement (M), and a cover (18) operable to cover and open the first opening (16*a*).

10 Claims, 13 Drawing Sheets

(a)

(b)

(c)

(a)

(b)

LASER ULTRASONIC PROPERTY MEASUREMENT APPARATUS

TECHNICAL FIELD

The present invention relates to an apparatus in which a surface of an object of measurement is irradiated with laser light to thereby excite ultrasonic waves in the object of measurement, for detection of variations in waveform of ultrasonic waves propagating in the object of measurement, to implement measurements of properties of the object of measurement based thereon.

BACKGROUND ART

There has been a property measuring method of a laser ultrasonic type known as a method of measuring properties of metal, such as a crystal grain size.

This property measuring method of laser ultrasonic type irradiates an object of measurement by laser light to excite ultrasonic waves in the object of measurement, and measures variations in waveform of such ultrasonic waves, as they are propagating in the object of measurement, to thereby implement measurements of properties of the object of measurement.

There will be described the principle of the above-noted measuring method with reference to FIG. 13. From an exciting laser light source 82, pulse laser light is shot to an obverse side of an object of measurement M (typically, a metal), causing small-scale explosions (ablations) on the object of measurement M, thereby producing pulsed ultrasonic waves in the object M. Such ultrasonic waves propagate in the object of measurement M, attenuating, and appear as fine vibrations at a reverse side of the object of measurement M. To the reverse side, probing laser light is shot from a probing laser light source 84, and between reflected light of that and reference light, interferences are caused, using an interferometer 86, whereby fine vibrations appearing at the reverse side of the object of measurement M can be read as voltage signals. Those voltage signals are input to a computer 88, and waveform-analyzed, thereby obtaining crystal grain sizes, Young's modulus, Lankford value, etc.

Such being the case, by use of a property measurement apparatus of laser ultrasonic type, properties of an object of measurement M can be measured in a noncontact manner, enabling measurements even for objects of measurement with hot temperatures.

Further, the property measurement apparatus of laser ultrasonic type allows ultrasonic vibrations to be excited in an object M at high frequencies ranging several tens to several hundreds MHz, and is preferable in particular for measurements of crystal grain sizes of a rolled steel plate.

And now, such a laser ultrasonic measurement apparatus as described needs to employ laser light having sufficient intensities for irradiation of an object of measurement with exciting laser light to excite small-scale explosions (ablations) on a surface of the object of measurement, and for irradiation of the object of measurement with probing laser light to enable measurements by an interferometer. In particular, as a laser device for emission of exciting laser light, there should be a high-power laser device of Class 4 or more prescribed in the JIS (Japanese Industrial Standards C 6802 (1991) "Radiation Safety Standard for Laser Products").

For use of such a high-power laser device, intensities of, among others, scattered light and reflected light of laser should be sufficiently reduced for a secured safety of workers. Therefore, for laser ultrasonic measurement apparatuses in the past, which were used in most cases in a sealed unmanned laboratory by remote operations, it practically was impossible to implement an application to a production line of a rolled steel plate, for example.

As a method of using a laser ultrasonic apparatus elsewhere than sealed laboratories, there has been a defect inspection method disclosed in Japanese Patent Application Laid-Open Publication No. 2004-101189. In this inspection method, light shielding covers are used to cover simply optical paths of laser light and irradiated parts, for a safety of workers to be secured.

However, in application of this method, where light shielding covers have to be attached close to an object of measurement, production lines for a rolling process of metal or the like might suffer from a difficulty to keep close attachment, for reasons such as that the object of measurement may have hot temperatures, that the object of measurement may move, and that in some cases the object of measurement may have uneven surfaces, with resultant leakage of scattered light of laser, reflected light, or such, as an issue.

Further, close attachment of light shielding covers to an object of measurement might cause among others surface flaws of the object of measurement, reduced temperatures of the object of measurement, and worn light shielding covers, as a disadvantage.

The present invention has been devised to solve such problems, and it is an object thereof to provide a laser ultrasonic property measurement apparatus without the need of close attachment of light shielding covers to an object of measurement, thus allowing for a facilitated transfer of an object of measurement to be put in or taken out.

Further, it is another object of the present invention to provide a laser ultrasonic property measurement apparatus allowing for a sufficient reduction in intensity of leaking scattered light or reflected light of laser, even for an object of measurement greater than a light blocking structure.

DISCLOSURE OF INVENTION

To achieve the above-noted object, a first mode of the present invention provides a laser ultrasonic property measurement apparatus comprising: a transmitter (12, 32) configured to shoot exciting laser light to an object of measurement (M) to excite ultrasonic waves in the object of measurement (M); a receiver (14) configured to shoot probing laser light to the object of measurement (M) to receive reflected light of probing laser light from the object of measurement (M) for detection of ultrasonic waves; a light blocking structure (16, 26, 36, 46, 47) configured with a first opening (16a, 26a, 36a, 46a, 47a) allowing the object of measurement (M) to pass therethrough and adapted to accommodate the object of measurement (M); and a cover (18) adapted to cover and open the first opening (16a, 26a, 36a, 46a, 47a).

Further, a second mode of the present invention provides a laser ultrasonic property measurement apparatus according to the first mode, wherein the light blocking structure (16, 26, 36, 46, 47) comprises at least one second opening (16b, 26b, 36b, 46b, 47b) oriented in a perpendicular direction to an opening direction of the first opening (16a, 26a, 36a, 46a, 47a), and at least one light blocking plate (P1 to P4) disposed between the second opening (16b, 26b, 36b, 46b, 47b) and a location to be irradiated by exciting laser light.

A third mode of the present invention provides a laser ultrasonic property measurement apparatus according to the second mode, wherein a length (L) of the light blocking structure (16, 26, 36, 46, 47) and a first gap distance (h)

between the light blocking plate (P1 to P4) and the object of measurement (M) are determined in dependence on an intensity of scattered light directly leaking from the second opening (16b, 26b, 36b, 46b, 47b), a thickness of the object of measurement (M), and an amount of warpage of the object of measurement (M), and the location of the light blocking plate (P1 to P4) is determined in dependence on a ratio between the first gap distance (h) and a second gap distance (H) between the light blocking structure (16, 26, 36, 46, 47) and the object of measurement (M).

A fourth mode of the present invention provides a laser ultrasonic property measurement apparatus according to any one of the first to third modes, further comprising: a detector (S) configured to detect the cover (18) being open to the first opening to output a detection signal; and a shutter (13) configured to receive a detection signal to prevent exciting laser light from being emitted.

A fifth mode of the present invention provides a laser ultrasonic property measurement apparatus according to any one of the first to the fifth, wherein the transmitter (12) is configured to be fixed so as to fit in to the light blocking structure (26).

A sixth mode of the present invention provides a laser ultrasonic property measurement apparatus according to any one of the first to fifth modes, wherein the light blocking structure (16, 26, 36, 46, 47) comprises a carrying roller (46c) configured to carry the object of measurement (M).

A seventh mode of the present invention provides a laser ultrasonic property measurement apparatus according to any one of the second to sixth modes, further comprising: two second openings (16b, 26b, 36b, 46b, 47b) provided for the light blocking structure (16, 26, 36, 46, 47); a feeder (52) arranged to face one of the second openings (16b, 26b, 36b, 46b, 47b) and configured to feed the object of measurement (M) to the light blocking structure (16, 26, 36, 46, 47); and an acceptor (54) arranged to face the other of the second openings (16b, 26b, 36b, 46b, 47b) and configured for cooperation with the feeder (52) to provide a tension to the object of measurement (M) being fed from the light blocking structure (16, 26, 36, 46, 47).

An eighth mode of the present invention provides a laser ultrasonic property measurement apparatus according to the seventh mode, wherein the feeder (52) is configured for a concurrent function to roll the object of measurement (M).

A ninth mode of the present invention provides a laser ultrasonic property measurement apparatus according to the seventh or the eighth mode, wherein the acceptor (54) comprises a winder (54) configured to wind up the object of measurement (M) being fed from the light blocking structure (16, 26, 36, 46, 47).

A tenth mode of the present invention provides a laser ultrasonic property measurement apparatus according to any one of the first to seventh modes, comprising an unloader (5) configured to push forward the object of measurement (M) toward the first opening (16a, 26a, 36a, 46a, 47a).

An eleventh mode of the present invention provides a laser ultrasonic property measurement apparatus according to any one of the first to eighth modes, further comprising a mover (7) configured to move the object of measurement in an opposite direction to an opening direction of the first opening (16a, 26a, 36a, 46a, 47a).

According to the present invention, it is unnecessary to attach a light blocking structure and an object of measurement close to each other, thus allowing provision of a laser ultrasonic property measurement apparatus with a facilitated transfer of an object of measurement to be put in or taken out. It is possible to provide a laser ultrasonic property measurement apparatus allowing for a sufficient reduction in intensity of leaking scattered light or reflected light of laser, even for an object of measurement greater than a light blocking structure.

BEST MODE FOR CARRYING OUT THE INVENTION

Figure 1:
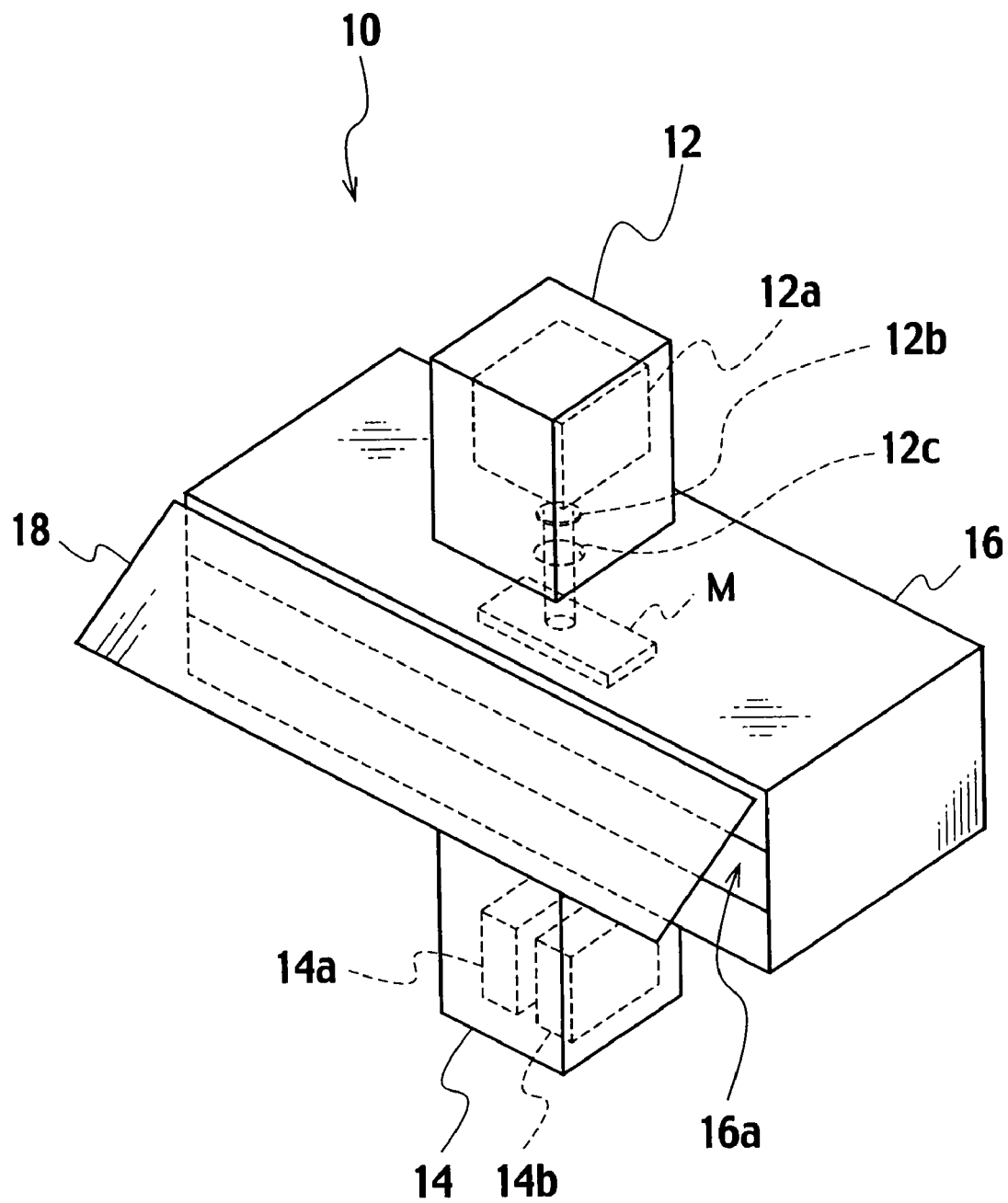
FIG. 1 is a schematic diagram of a laser ultrasonic property measurement apparatus according to a first embodiment of the present invention.

There will be described embodiments of the present invention into details, with reference to the accompanying drawings. In the drawings, like members or elements are designated by like reference characters, and redundant description thereon is omitted. Any accompanying drawing is a simple schematic presentation of a laser ultrasonic property measurement apparatus according to an individual embodiment. And, it is noted that, between components, ratios or the like are not always represented as actually designed.

First Embodiment

FIG. 1 is a schematic diagram of a laser ultrasonic property measurement apparatus (referred below simply to "measurement apparatus") according to the first embodiment of the present invention. As illustrated in the figure, according to the first embodiment, a measurement apparatus 10 includes a transmitter 12, a receiver 14, a light blocking structure 16, and a cover 18.

The transmitter 12 shoots exciting laser light to an object of measurement M (referred below to "object M"), having ultrasonic waves excited in the object M. The transmitter 12 includes a laser light source 12a, an optical system 12b, and a shooting window 12c, as illustrated in FIG. 1. The laser light source 12a emits pulse laser light that has, as exciting laser light, sufficient energy to cause ablations at an obverse side of the object M. The laser light source 12a may be an yttrium aluminum garnet (YAG) laser device (wavelength 1,064 nm) for example, without restriction thereto. The optical system 12b admits transmission of exciting laser light emitted from the laser light source 12a, and controls a beam diameter thereof and a shooting direction. Specifically, the beam diameter is determined in accordance with, among others, a capacity (energy) of the laser light source 12a and a surface condition of the object M. Laser light transmitted through the optical system 12b is emitted, through the shooting window 12c, into the light blocking structure 16.

The receiver 14 shoots probing laser light to the object M, and receives reflected light of probing laser light from the object M, for detection of ultrasonic waves. The receiver 14 includes a laser light source 14a, an interferometer 14b, and a shooting window (not shown). The laser light source 14a emits continuous laser light as probing laser light. The laser light source 14a may be a YAG laser device for example, without restriction thereto. It is noted that the higher the intensity of probing laser light is, the clearer ultrasonic waves excited in the object are detectable, and it is preferable for the laser light source 14a to emit laser light with a high intensity within a range where it causes no ablations at a reverse side of the object M. For the interferometer 14b, there are various employable interferometers, including a two-wavelength mixing interferometer using a photorefractive crystal, or a Fabry-Perot interferometer excellent in frequency characteristic, allowing a stable measurement even if the side (the reverse side of the object M) to be irradiated by probing laser light is coarse. The shooting window of the receiver 14 is configured to admit transmission of probing laser light, and transmission of reflected light thereof.

The light blocking structure 16 is made in the form of a box by a metal, to accommodate the object M therein. The light blocking structure 16 may be formed by such a method that is a welding, casting, forging, or molding. The light blocking structure 16 has an opening 16a for the object M to be loaded or unloaded therethrough, a through hole (not shown) coincident with the shooting window 12c of the transmitter 12, and a through hole (not shown) coincident with the shooting window 12c of the receiver 14. Those through holes admit transmission of respective laser light, and preferably should be as small as possible so far as they do not interfere with the receiver 14 collecting reflected light. Further, as illustrated in FIG. 1, the transmitter 12 and the receiver 14 are directly fixed on the light blocking structure 16, which is more preferable from the viewpoint of preventing leakage of laser light. Still more, to prevent reflection of exciting laser light and probing laser light, the inside of light blocking structure 16 may preferably be treated to be low in reflectivity at wavelengths of those laser light. Specifically, the inside may be useful if painted in black.

The cover 18 is configured so that it can cover the opening 16a, and this is openable by hinge joints (not shown) the light blocking structure 16 has above the opening 16a. The cover 18 is adapted, in a close state, to prevent laser light from leaking outside from inside the light blocking structure 16, and in an open state, to allow a loading and an unloading of an object M through the opening 16a of the light blocking structure 16. The cover 18 is open-close operable, manually or automatically. It is noted that in the first embodiment, the cover 18 is configured to vertically swing about the hinge joints provided above the opening 16a, while it may be horizontally swingable, instead. Further, the cover 18 may be composed not simply of a single panel, but also of tow or more plates. In this case, the paneled plurality may be open-close operable simply in part in accordance with a size of the object M. Further, the cover 18 may be a double swing panel composed of two plates. Still more, instead of using hinge joints, it may be open-close operable by a vertical or horizontal sliding.

The receiver 14 has a computer (not shown) electrically connected thereto, where on bases of voltage signals of ultrasonic waves detected at the receiver 14, a waveform analysis is performed, for acquisition of crystal grain sizes, Young's modulus, Lankford value, etc.

According to the configuration described above, pulse laser light is shot as exciting laser light from the transmitter 12 to an obverse side of an object M, causing small-scale explosions at the obverse side of object M, whereby ultrasonic waves are excited in the object M. Those ultrasonic waves propagate in the object M, attenuating, and appear as fine vibrations at a reverse side of this. On the other hand, continuous laser light is shot as probing laser light from the receiver 14 to the reverse side of the object M. Shot laser light has reflected light, which is employed by the interferometer 14a in the receiver 14 to cause interferences with reference light, so that fine vibrations appearing at the reverse side of object M are sampled as voltage signals. After that, those voltage signals are analyzed, acquiring, among others, the object M's crystal grain size, Lankford value, and the like.

According to the first embodiment, in the measurement apparatus 10, laser light as shot to an object M and reflected or scattered is prevented from leaking outside, by the light blocking structure 16 that has an opening 16a and the cover 18 that covers the opening 16a, thus allowing for a secured safety of workers. The measurement apparatus 10 has an advantage that the cover 18 is operable to open, thereby allowing for a facilitated loading and unloading of an object M through the opening 16a of the light blocking structure 16. Further, there is no need of provision of members to be attached close to an object M, unlike simply covering, among others, optical paths of laser light and irradiated parts with light shielding members. It therefore is possible to prevent occurrences of surface flaws of the object M, having its surfaces worn, etc. Still more, possible elongate distances between the transmitter 12 and an object M enable implementation of measurements even if the object M has hot temperatures.

In particular for measurements of crystal grain sizes of a rolled steel plate, it is noted that preferably ultrasonic vibrations of high frequencies ranging several tens to several hundreds MHz should be excited in the object M, and from this viewpoint, it is desirable to employ laser light for excitation and reception of ultrasonic waves. However, it also is possible to employ a piezoelectric or electromagnetic ultrasonic-wave generating device or any sort of ultrasonic wave transmission-reception means for transmission or reception, whichever is consistent with measurement environment and measurement items.

It is noted that in the measurement apparatus 10 according to the first embodiment, the transmitter 12 and the receiver 14 are arranged in a vertical relationship, without restriction thereto, and they may be juxtaposed, with an intervening object in between. Further, the receiver 14 may be disposed so as to irradiate an identical side with exciting laser light and probing laser light.

Second Embodiment

Figure 2:
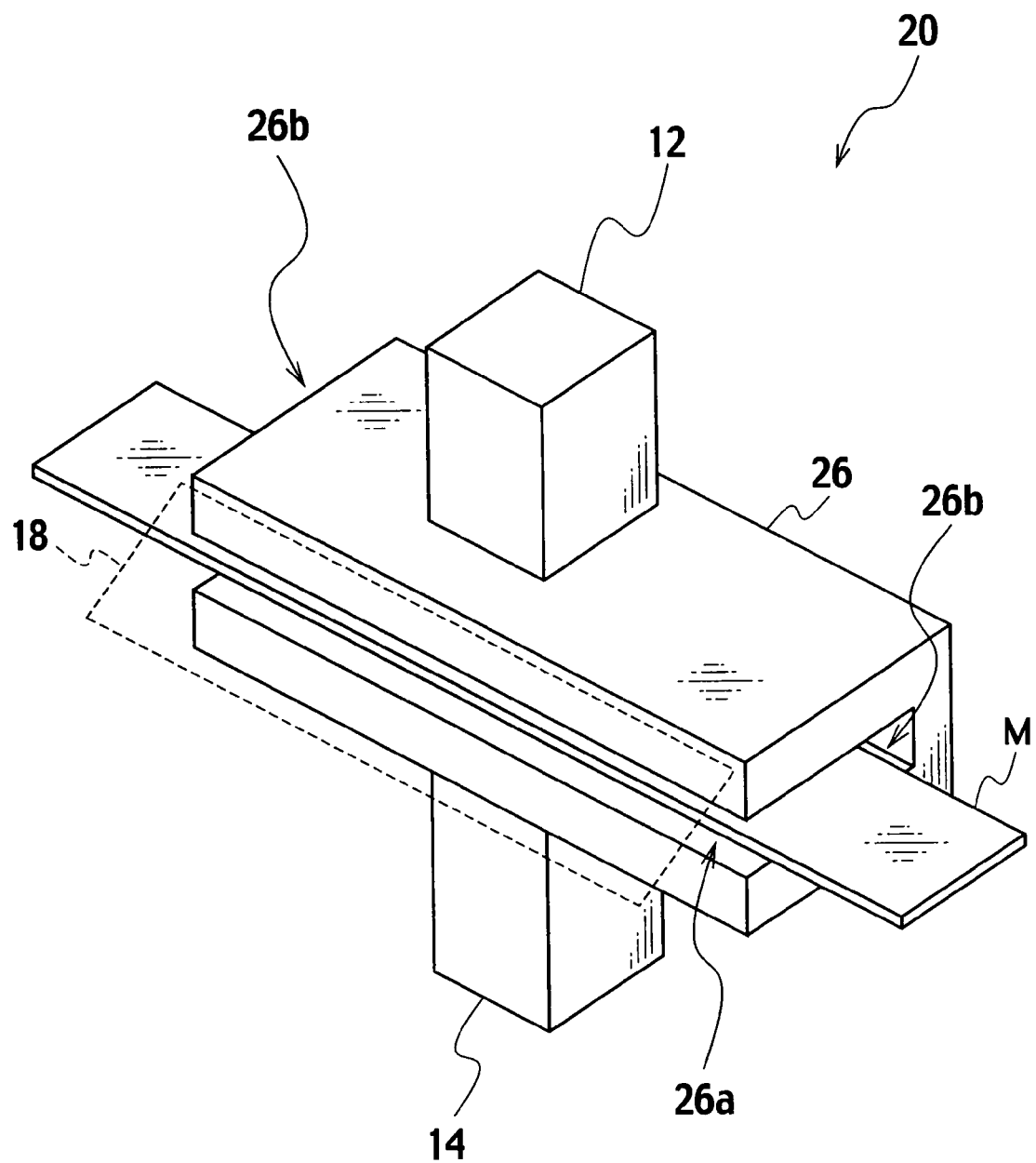
FIG. 2 is a schematic diagram of a laser ultrasonic property measurement apparatus according to a second embodiment of the present invention.

FIG. 2 is a schematic diagram of a measurement apparatus according to the second embodiment of the present invention. As illustrated in the figure, according to the second embodiment, a measurement apparatus 20 includes a transmitter 12, a receiver 14, a light blocking structure 26, and a cover 18. The light blocking structure 26 is different from the light blocking structure 16 of the first embodiment in that it has additional openings else than an opening 26a corresponding to the opening 16a of the light blocking structure 16. That is, the light blocking structure 26 has openings 26b disposed at both ends of the opening 26a and oriented in directions perpendicular to an opening direction of the opening 26a. The openings 26b have dimensions allowing an object M to pass therethrough without contacting the light blocking structure 26, and as is apparent from FIG. 2, it is possible to load and unload the object M through the openings 26b.

The light blocking structure 26 has, as illustrated in FIG. 3(b), a plurality of light blocking plates P1 to P4 arranged between the openings 26a and an irradiated point of laser light shot to the object M, so that they traverse traveling directions of scattered light, specifically at right angles relative to a surface of the light blocking structure 26 where the object M is placed, in this embodiment. Those light blocking plates P1 to P4 function to reflect scattered light of exciting laser light, and reflected light, in an attenuating manner.

Referring now to FIG. 3(a) to (c), description is made of scattered light of exciting laser light I.

As illustrated in FIG. 3(a), exciting laser light I is shot perpendicularly to an irradiated point A, from above the object M, and reflected light R and scattered light S are resulted, as shown by arrows. The arrows have their lengths generally representing intensities of reflected light R and scattered light S. Intensities of scattered light S are varied, depending on surface conditions such as a roughness of the object M, generally decreasing as a scatter angle θ (the angle to the surface of object M) decreases. That is, letting $I_0$ be an intensity of exciting laser light I, scattered light has an intensity $I_s$ represented by $$I_s = I_0 \times f(\theta). \tag{1}$$

FIG. 3(b) illustrates exemplary light paths, where scattered rays of light travel from the irradiated point A. As illustrated in the figure, scattered rays of light S1 to S4 are incident on and reflected by the light blocking plates P1 to P4, and thereafter, reflection is repeated several times. Further, in FIG. 3(b), scattered rays of light represented by light paths C are directly leaking outside, without being reflected by any light blocking plate. Assuming now increased lengths L of light blocking structure 26 (as lengths from an incidence point of exciting laser light I to the openings 26b of the light blocking structure 26) and a decreased gap distance h the light blocking plates P1 to P4 have to the object M, it so follows that simply those rays of scattered light having decreased scatter angles θ and decreased intensities leak outside along light paths C, thus allowing for a significant minimized intensity of scattered light leaking outside. In this respect, the distance h should be set within a certain range of dimensions where at least the object M is kept from hitting. Hence, the distance h is set to a value taking into account, among others, a plate thickness and a plate warpage amount of object, with a margin added thereto for allowance, that is, $$h = \text{plate thickness} + \text{warpage amount} + \text{allowance margin}. \tag{2}$$

As illustrated in the figure, this is identical to a height of the openings 26b in the second embodiment.

Then, a length L of the light blocking structure 26 is determined so that such scattered light as directly leaking outside has a sufficiently small intensity, that is, so as to meet the following condition:

$$I_{UL} \geq I_0 \times f(\theta_{MAX}), \tag{3}$$

where $I_{UL}$ is an upper limit of intensity permissible to scattered light directly leaking outside, as a value to be determined in accordance with a state of installation and conditions of use of the measurement apparatus 20, and $\theta_{MAX}$, a maximum value of angles defined between the object M and rays of scattered light permitted to directly leak outside.

This is solved for θ, obtaining $$\theta_{MAX} \leq f^{-1}(I_{UL}/I_0). \tag{4}$$

This $\theta_{MAX}$ is employable to determine the length L of light blocking structure by $$L = h / \tan \theta_{MAX}. \tag{5}$$

In this respect, the length L may be decided in consideration of a state of installation, production cost, etc of the measurement apparatus 20.

Figure 4:
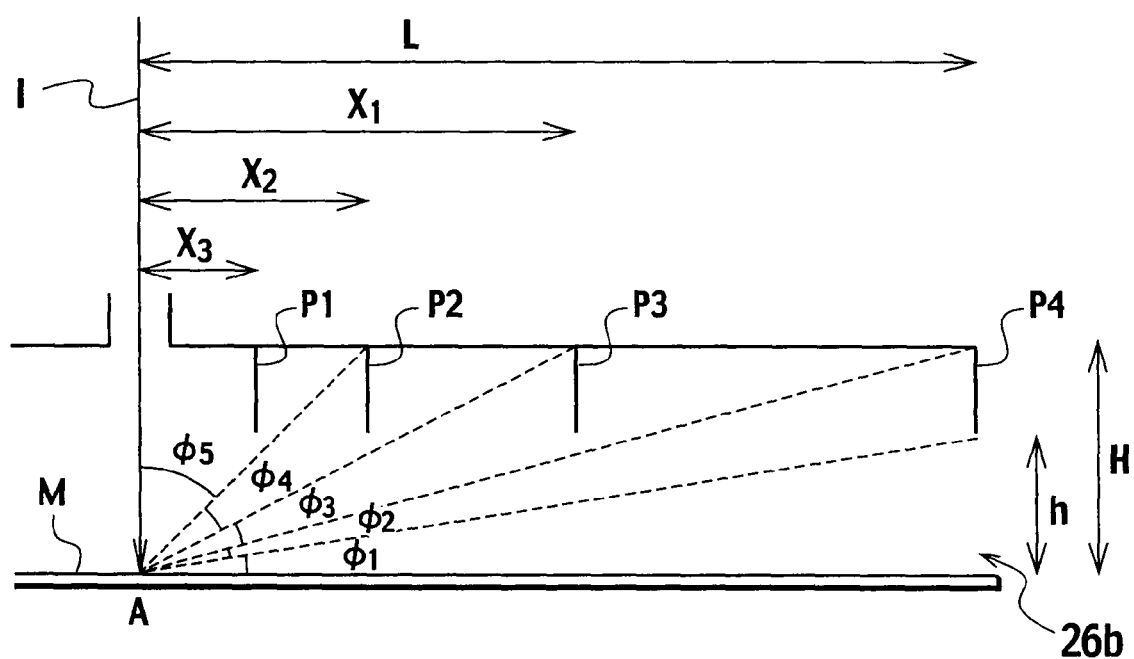
FIG. 4 is a diagram illustrating positioning light blocking plates of the measurement apparatus shown in FIG. 2.

FIG. 4 is a diagram illustrating an exemplary method of determining installation positions of the light blocking plates P1 to P4. Among rays of scattered light from the point A, those rays of scattered light S having scatter angles belonging to a range φ5, as well as rays of reflected light R, are kept from striking on light blocking plates P1 to P4, and have substantially upward directions of travel, so they are repeatedly reflected by and between an inside region of the light blocking structure 26 and the object M, being absorbed gradually, and have sufficiently reduced intensities. Those rays of scattered light having scatter angles belonging to a range φ1 have intensities sufficiently reduced by adjustments of length L and distance h, as described above, so they give no problems, even if emitted outside, striking on no light blocking plates.

On the other hand, those rays of scattered light having scatter angles belonging to ranges φ2 to φ4 strike on light blocking plates P1 to P4 disposed as will be described below, changing directions of travel, and are repeatedly reflected, thus having sufficiently reduced intensities.

In FIG. 4, the light blocking plate P4 is provided in a position corresponding to L as determined by the expression (5), that is, at an opening end of the light blocking structure 26. The light blocking plate P4 thus constitutes part of the light blocking structure 26. The light blocking plate P4 can reflect those rays of scattered light having scatter angles belonging to the range φ2, where these are greater than in the range φ1, making those travel in opposite directions to an opening 26b. Therefore, such rays of scattered light are reflected many times, having reduced intensities.

Next, the light blocking plate P3 is provided in a position x1 (FIG. 4), so that it can reflect those rays of scattered light having scatter angles belonging to the range φ3. The position x1 is easily calculable from the similarity relationship of triangle, and given by $$x1 = L \times h / H, \tag{6}$$

where L is the above-noted length of the light blocking structure 26, H, an inside height of the light blocking structure 26, and h, the gap distance between the light blocking plates P1 to P4 and the object M.

Likewise, the light blocking plate P2 has a position x2, as it is provided in position so that it can reflect those rays of scattered light having scatter angles belonging to the range φ4, making those travel in opposite directions to the opening 26b. The position x2 of light blocking plate is obtained by $$x2 = x1 \times h/H. \quad (7)$$

Also for the light blocking plate P1, a position x3 is likewise given by $$x3 = x2 \times h/H. \quad (8)$$

For a configuration of light blocking structure having light blocking plates at no more than opening ends thereof, as illustrated by light paths S10 and S11 in FIG. 3(c), rays of scattered light from the irradiation point A (in particular, those rays of scattered light having scatter angles belonging to ranges from θ3 to θ4 inclusive) are reflected by and between an inside of the light blocking structure 26 and the object M a relatively small number of times (once or twice, for example) to reach the openings, and emitted outside, as they are left as they might have insufficiently attenuated intensities with a threat to worker's safety. However, according to the second embodiment, the measurement apparatus 20 allows for a secured safety of workers, as rays of scattered light have intensities sufficiently attenuated by the light blocking plates P1 to P4, even when they leak from the openings 26b.

Figure 3:
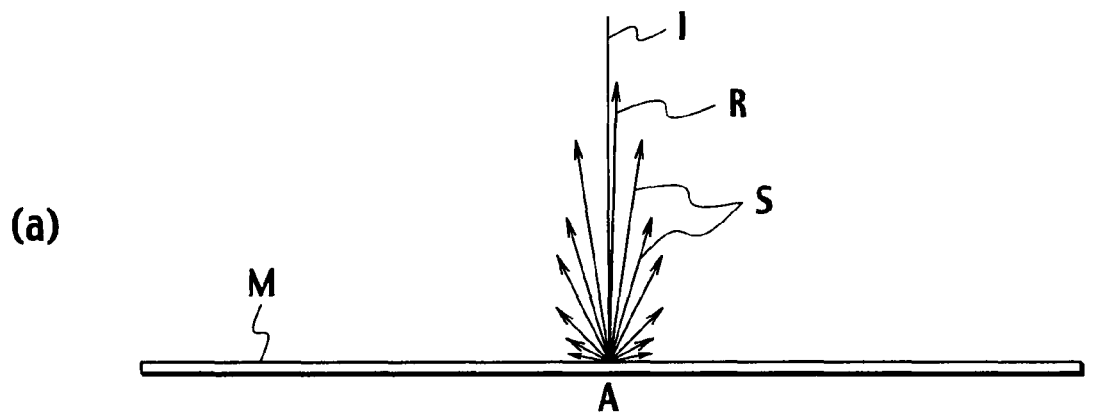
FIG. 3(a) is a schematic illustration of an object of measurement irradiated with exciting laser light, reflected light, and scattered light, (b), an elevation of light blocking plates of the laser ultrasonic property measurement apparatus shown in FIG. 2, and (c), a schematic illustration of light paths of scattered rays of light.
Figure 3:
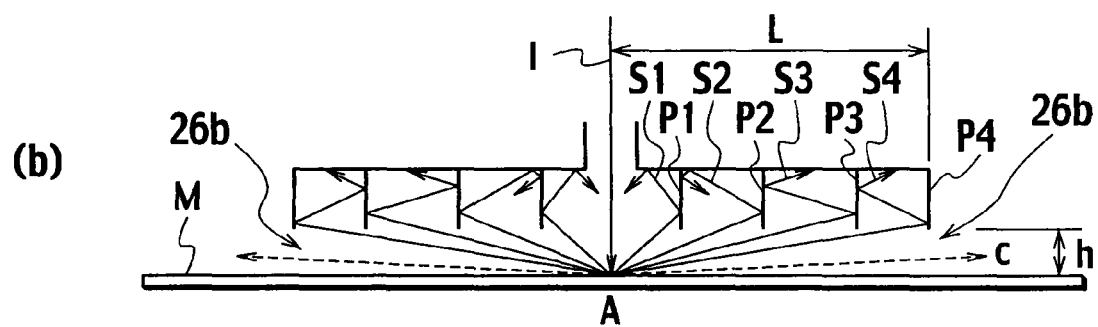
Figure 3:
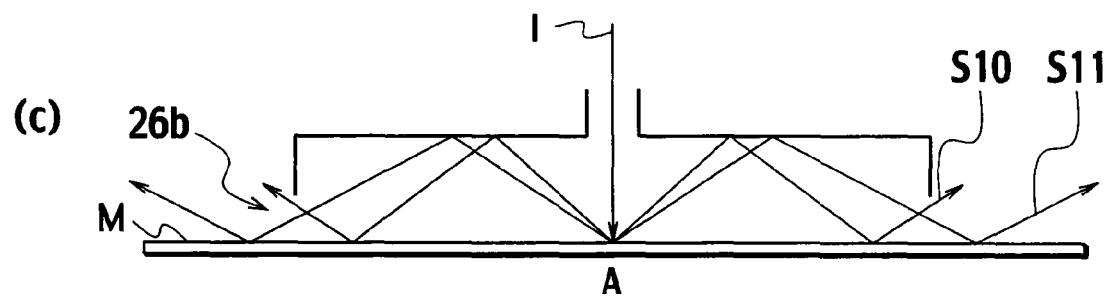

Although description has been made for a set of four light blocking plates with reference to FIG. 3 and FIG. 4, it also is possible to provide a set of greater number of light blocking plates to attenuate scattered light the more effectively. The number of light blocking plates may be properly determined in consideration of intensity, cost, and the like of exciting laser light to be used, as matter of course.

According to the second embodiment above, in the measurement apparatus 20, a light blocking structure 26 has openings 26b opening in perpendicular directions to an opening direction of an opening 26a to be covered with a cover 18, and an object M can be loaded and unloaded therethrough, allowing even for a long object M to be measured without being cut. The openings 26b are provided with no members corresponding to the cover 18, but the light blocking structure 26 has therein sets of light blocking plates P1 to P4 interposed between the openings 26b and an optical path as a hole 12c, whereby rays of scattered light are reflected a plurality of times, having attenuated intensities, so scattered light leaking outside can be sufficiently reduced.

Although an embodiment has been illustrated for a pair of openings 26b in the second embodiment, it may well be for a single opening 26b. Even in this case, there may be a plurality of light blocking plates interposed between an irradiation point of exciting laser light and the opening 26b, allowing for sufficiently reduced intensities of rays of scattered light leaking outside.

Third Embodiment

Figure 5:
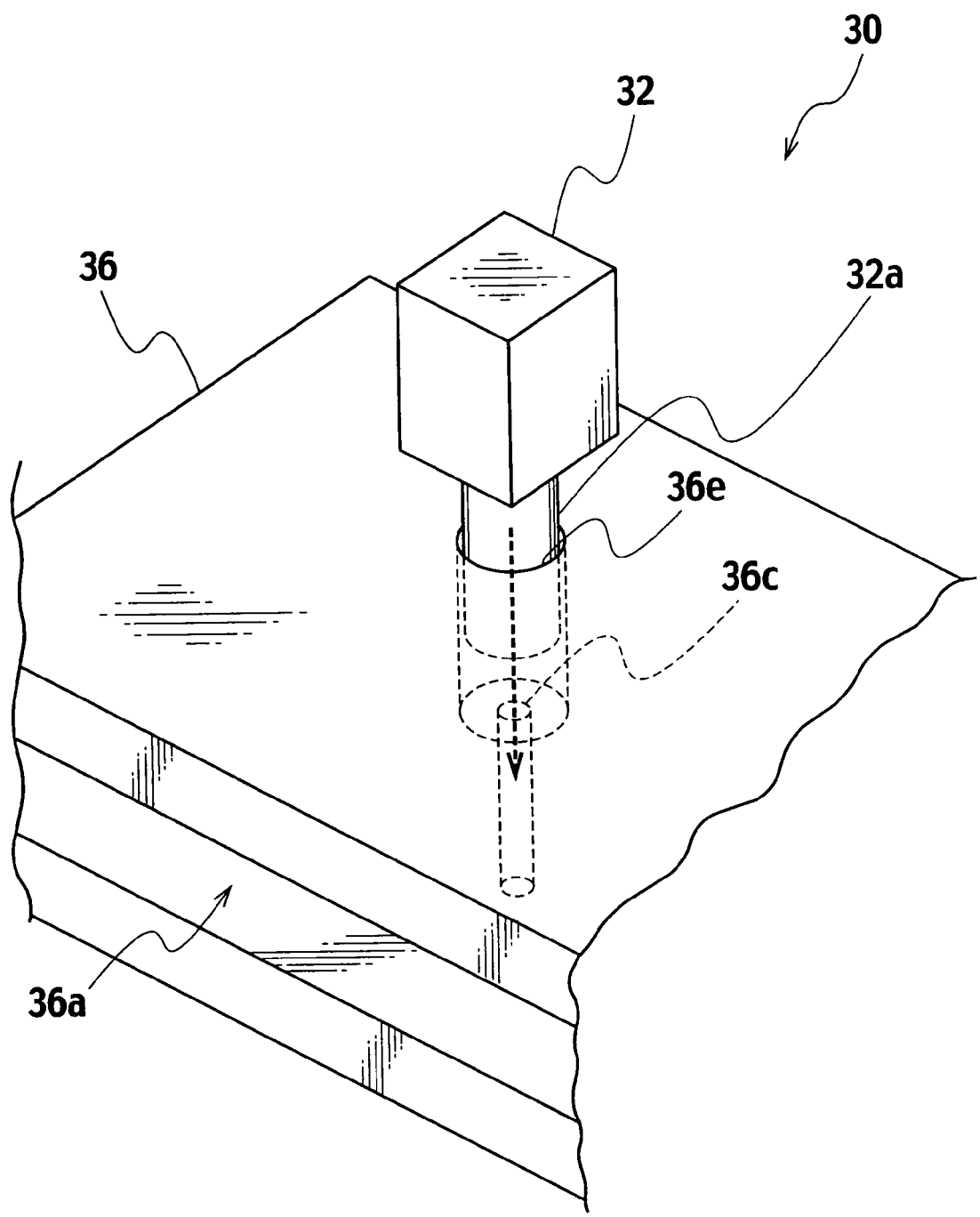
FIG. 5 is a schematic partial view of a laser ultrasonic property measurement apparatus according to a third embodiment of the present invention.

According to the third embodiment, a measurement apparatus is configured to be identical to the measurement apparatus 10 according to the first embodiment, except for a transmitter and a light blocking structure modified in part. FIG. 5 is a schematic partial view about the modification of the measurement apparatus according to the third embodiment of the present invention.

As illustrated in the figure, a transmitter 32 has a protrusion 32a, and a light blocking structure 36 has a depression 36e. The protrusion 32a has a hollow cylindrical shape, and exciting laser light is shot through inside. The depression 36e is shaped circular, with an inside diameter adjusted for the transmitter 32 to be fixed with a non-excessive play when the protrusion 32a is inserted into the depression 36e. The depression 36e has, at a substantially central region of the bottom thereof, a through hole 36c formed therein for exciting laser light from the transmitter 32 to pass therethrough.

By such the configuration, the transmitter 32 is fixed to the light blocking structure 36, with the protrusion 32a inserted inside the depression 36e, allowing exciting laser light to pass through inside the protrusion 32e and the through hole 36c to irradiate an object.

It is noted that the transmitter 32 has an identical configuration to the transmitter 12, except for provision of the protrusion 32a. Also the light blocking structure 36 has an identical configuration to the light blocking structure 16 or the light blocking structure 26, including provision of, among others, an opening 36a and openings 36b (FIG. 6(a)), except for provision of the depression 36e.

Figure 6:
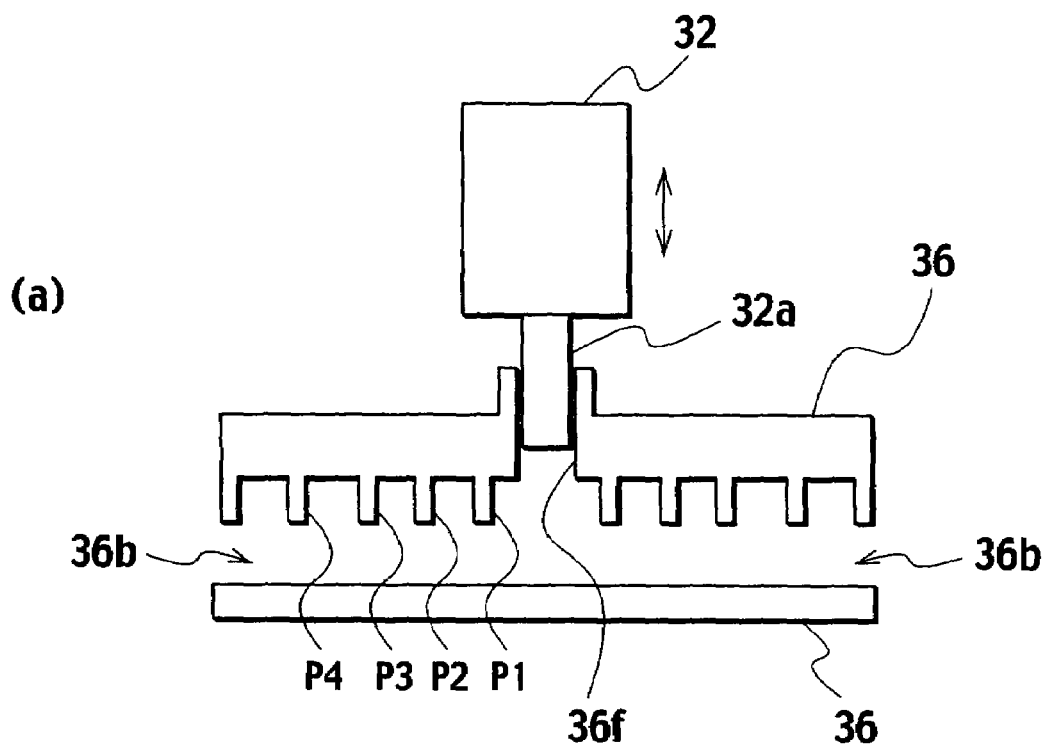
FIG. 6(a) is a sectional view of a laser ultrasonic property measurement apparatus according to a modification of the third embodiment, and (b), a diagram illustrating a fit-in length.
Figure 6:
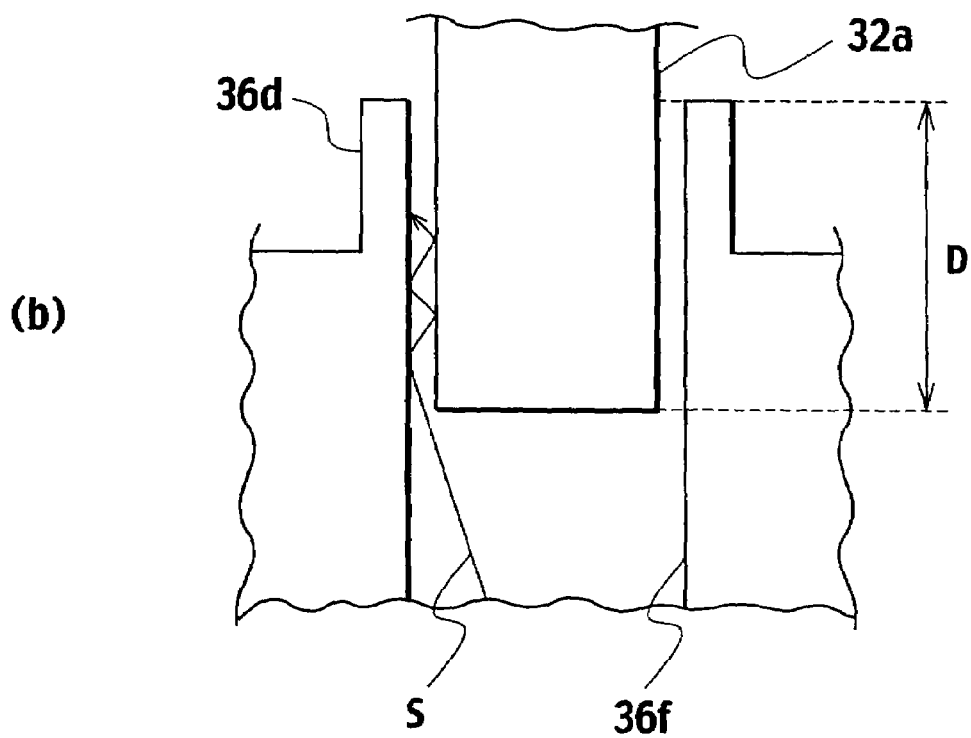

As illustrated in FIG. 6(a), the light blocking structure 36 may have, instead of the depression 36e, a through hole 36f for the protrusion 32a to fit therein. In this case, for the depression 32a or the through hole 36f, a fit length D (refer to FIG. 6(b)) is determined so that, upon irradiation of an object (not shown) by exciting laser light from the transmitter 32, rays of reflected light and scattered light S are reflected in a gap between the depression 32a and the hole 36f a plurality of times, attenuating to or below a desirable intensity. The intensity of scattered light is variable depending on the object's surface roughness, scattering directions, etc, and preferably, an adequate fit length D should be experimentally determined in advance. It is noted that, as illustrated in FIG. 6(b), the light blocking structure 36 may be provided with an annular depression (or sleeve) 36d for adjustment of the length D.

By the above-noted configuration, the transmitter 32 can be fixed with ease to the light blocking structure 36. Further, independently of the light blocking structure 36, a distance between the transmitter 32 and the object may be adjusted (like a double arrow in FIG. 6(a)), allowing adjustment of a focus distance, for example, to be implemented free of adjustment of an optical system (not shown) of the transmitter 32. Further, the protrusion 32a may have an adequate play to the depression 36e or the through hole 36f, to thereby protect the transmitter 32 from occurrences of mechanical vibrations in the light blocking structure 36.

It is noted that although the protrusion 32a has been described as having a hollow cylindrical shape, and the depression 36e, as being shaped circular, they are in no way restricted to such shapes. The may have voluntary shapes, subject to an adequate fit in between. Further, the protrusion 32a, which is not restricted to a hollow, may be a solid, subject to provision of a through hole allowing laser light to pass through. In a configuration, a fit may be implemented between a protrusion provided on a light blocking structure 26 and a depression or through hole provided in a transmitter 12. In other words, implementations can do with one of protrusion and depression provided to a transmitter 32 and the other of protrusion and depression provided to a light blocking structure 36, providing a mutual fixing by a concavo-convex fit between the transmitter 32 and the light blocking structure 36.

It also is possible to provide the first or second embodiment with a protrusion 32a on the transmitter 14, and a depression or through hole at a reverse side of the light blocking structure 16.

Fourth Embodiment

Figure 7:
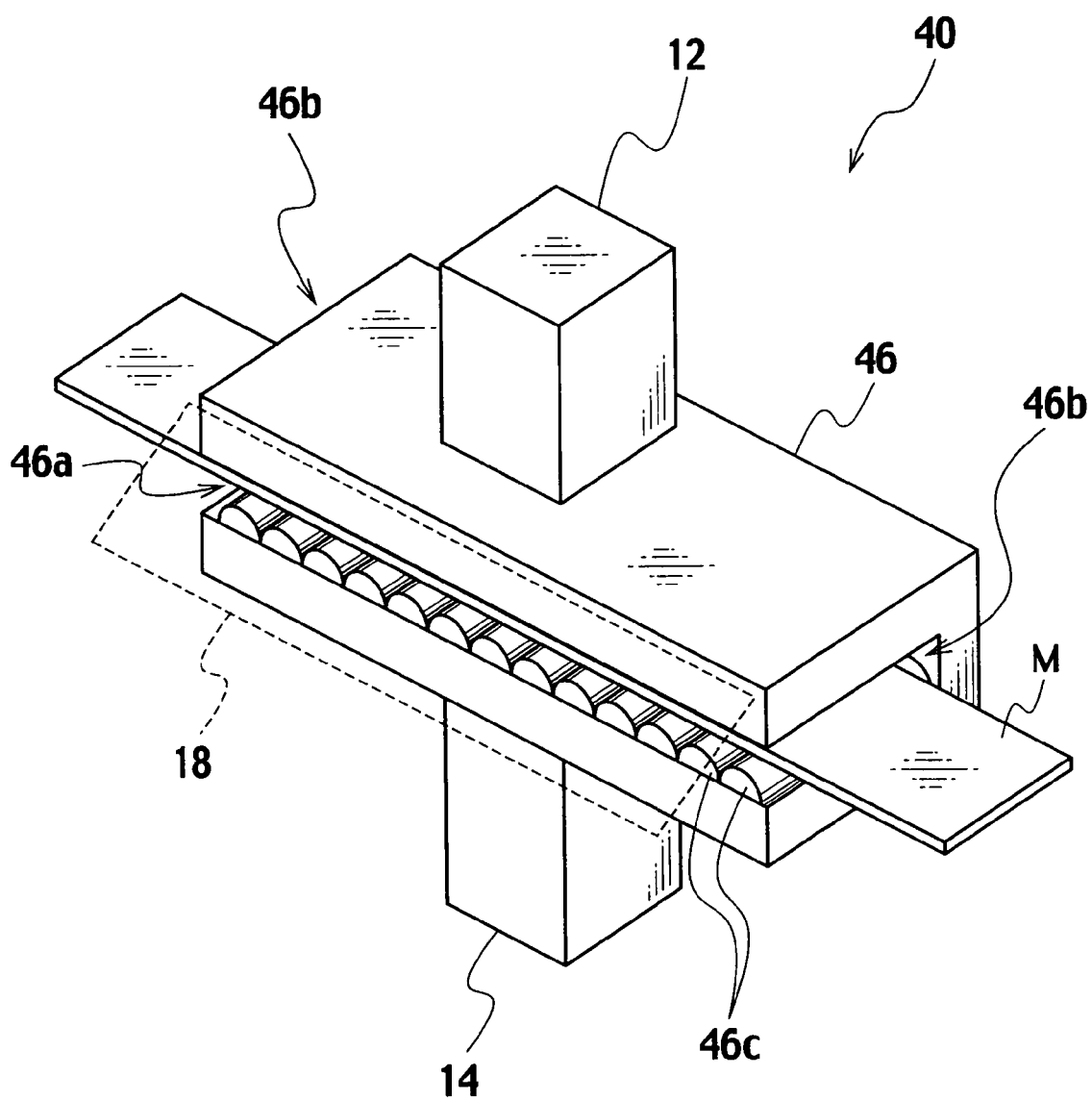
FIG. 7 is a schematic view of a laser ultrasonic property measurement apparatus according to a fourth embodiment of the present invention.

FIG. 7 is a schematic view of a measurement apparatus according to a fourth embodiment of the present invention. As illustrated in the figure, according to the fourth embodiment, a measurement apparatus 40 includes a transmitter 12, a receiver 14, a light blocking structure 46, and a cover 18. The light blocking structure 46 has an opening 46a corresponding to the opening 26a of the light blocking structure 26 in the second embodiment, and openings 46b corresponding to the openings 26b. In addition, the light blocking structure 46 has a plurality of conveyor rollers 46c. The conveyor rollers 46c are rotatable, electrically or manually, supporting an object M, transferring the object M by rolling actions. The conveyor rollers 46c are disposed so as not to interfere with light paths of probing laser light emitted from the receiver 14 and reflected light thereof. It is noted that the conveyor rollers 46c may be driven by pneumatic pressure, hydraulic pressure, etc.

According to the measurement apparatus 40, an object M can be loaded and unloaded through the openings 46a, allowing for implementing measurements at a plurality of measuring points to the object M being transferred by conveyor rollers 46c, from one of the openings 46a to the other. In addition, it is possible to implement, among others, loading the object M from the opening 46a, as well as unloading. In particular, when an object M is conveyed by conveyor rollers 46c, if it is disabled for some reason to take out the object M from either opening 46b, the opening 46a can provide a useful service to discharge the object M therefrom.

Fifth Embodiment

Figure 8:
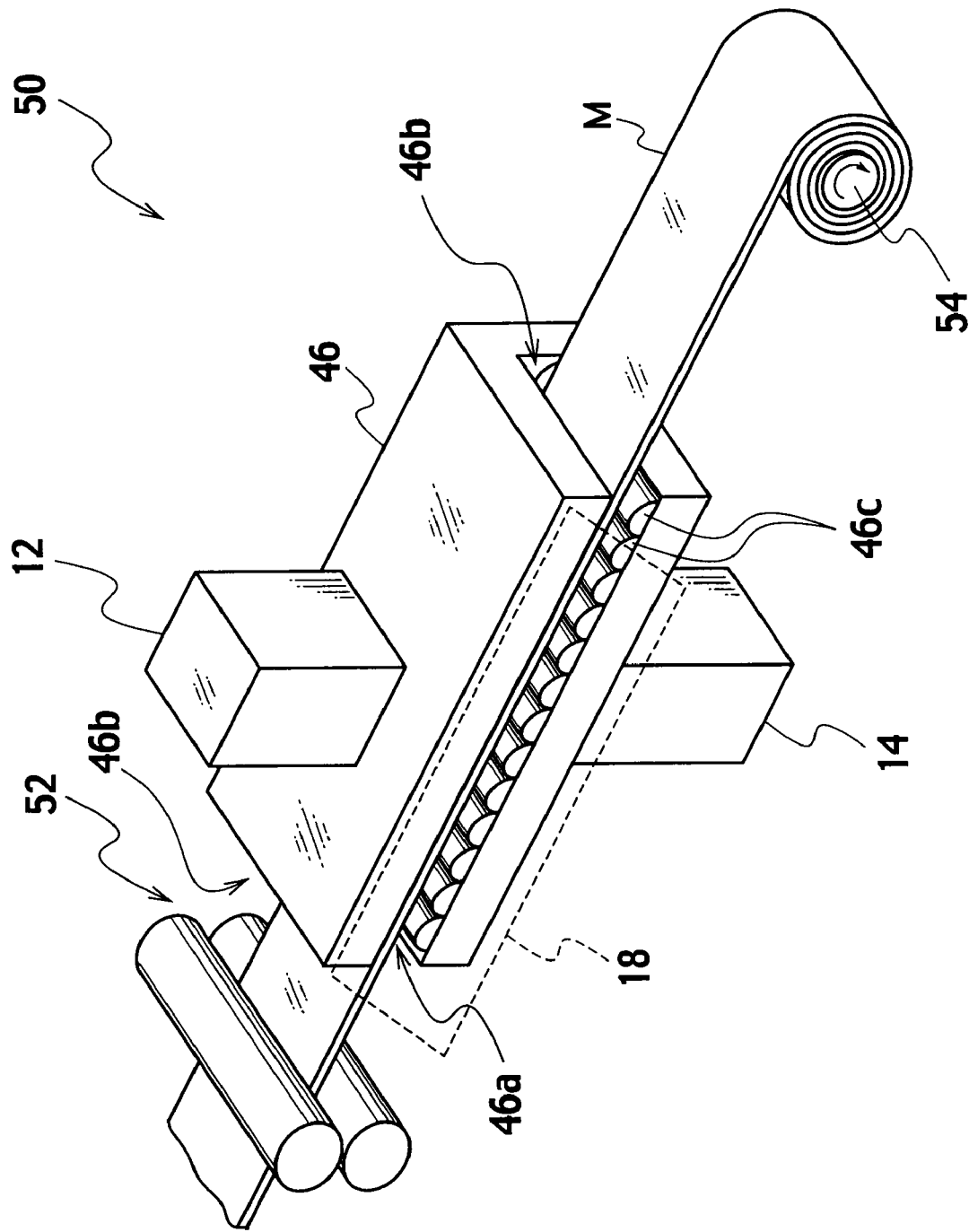
FIG. 8 is a schematic view of a laser ultrasonic property measurement apparatus according to a fifth embodiment of the present invention.

FIG. 8 is a schematic view of a measurement apparatus according to the fifth embodiment of the present invention. As illustrated in the figure, according to the fifth embodiment, a measurement apparatus 50 includes a transmitter 12, a receiver 14, a light blocking structure 46, a cover 18, a roller 52, and a winder 54. The roller 52 is disposed in position to face one of openings 46b, and serves for rolling, among others, a hot steel slab or billet, for example, to form a rolled strip, feeding this into the light blocking structure 46. In the light blocking structure 46, the rolled strip is fed to the other opening 46b by conveyor rollers 46c. The winder 54 is disposed in position to face the other opening 46b, and winds up on a roll the rolled strip as it has passed through the light blocking structure 46.

By such the configuration, rolled plates can be measured for crystal grain size and the like in the course of production. Further, for one or both of the winder 54 and the roller 52, the drive speed may be controlled, to thereby provide an adequate tension to a rolled strip passing through the light blocking structure 46, allowing for a smooth feed. In addition, given an adequate tension, the object M is adapted for favorable propagation of ultrasonic waves, as an effect to be provided.

The winder 54 may be substituted by pinch rollers, which may be accompanied by additional pinch rollers disposed between positions of winder 54 and opening 46b. In his case, tensions of rolled strip are controllable by pinch rollers.

Sixth Embodiment

Figure 9:
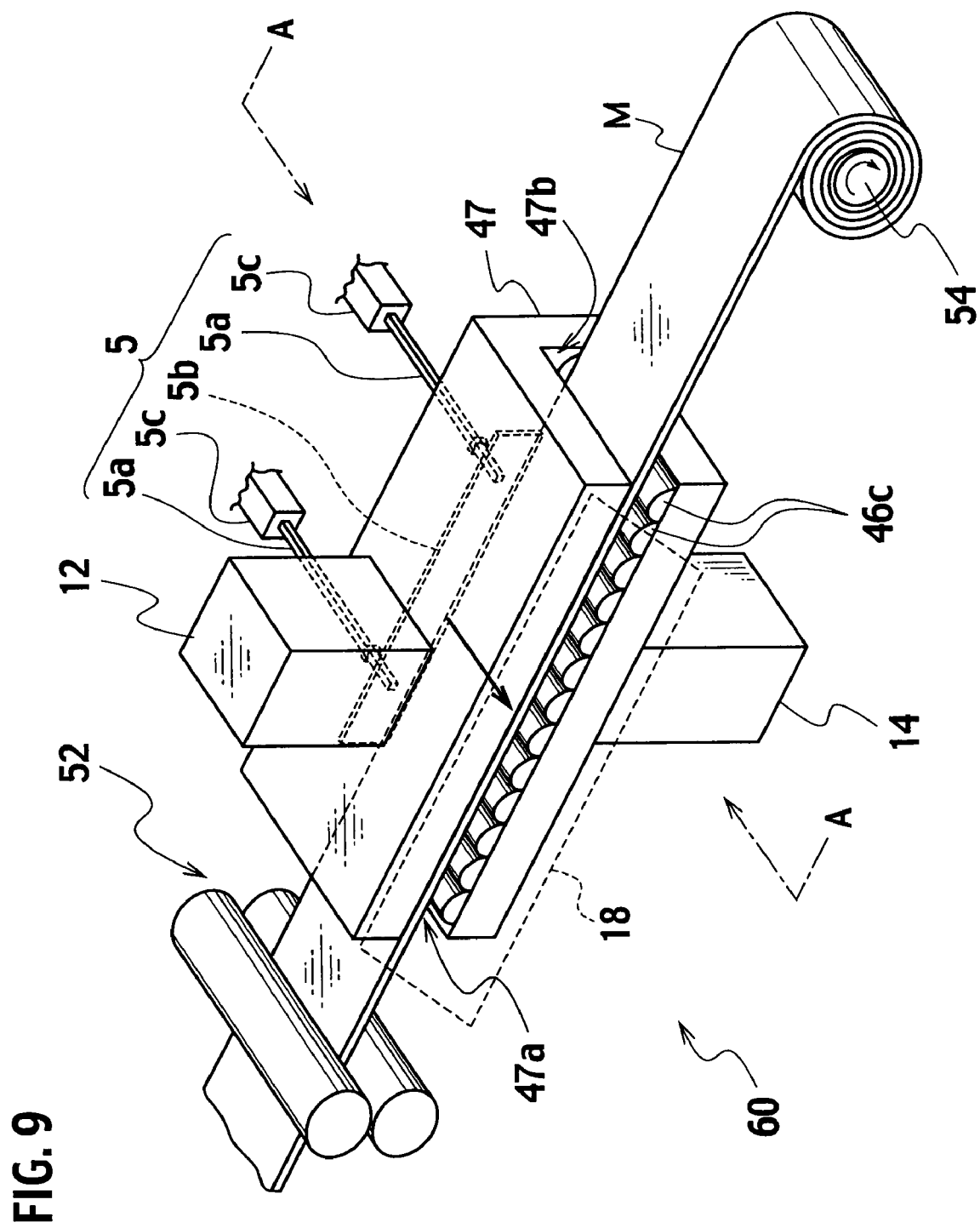
FIG. 9 is a schematic view of a laser ultrasonic property measurement apparatus according to a sixth embodiment of the present invention.
Figure 10:
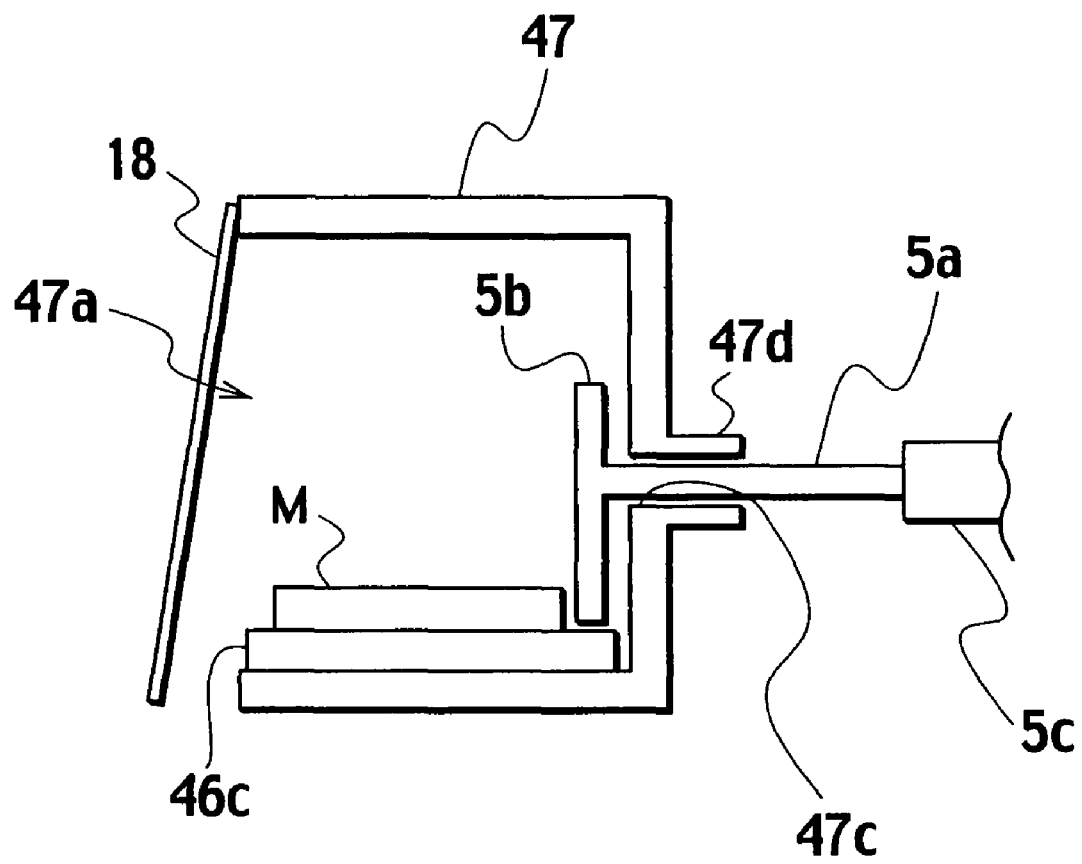
FIG. 10 is a sectional view of an A-A section of the laser ultrasonic property measurement apparatus shown in FIG. 9.

FIG. 9 is a schematic view of a measurement apparatus according to the sixth embodiment of the present invention. As illustrated in the figure, according to the sixth embodiment, a measurement apparatus 60 has a configuration in which an unloader 5 is added to the measurement apparatus 50 according to the fifth embodiment. The unloader 5 is made up by arms 5a, a push plate 5b, and hydraulic cylinders 5c. As illustrated in FIG. 10, the arms 5a are inserted into a light blocking structure 47, via through holes 47c provided at a back of the light blocking structure 47. The push plate 5b is attached to distal ends of the arms 5a as inserted. The push plate 5b is positioned on or above conveyor rollers 46c, and is adapted to push forward from aside an object M placed on conveyor rollers 46c. The arms 5a are connected at their other ends to the hydraulic cylinders 5c, so the hydraulic cylinders 5c are operable to make, through the arms 5a, the push plate 5b push forward the object M toward an opening 47a.

By the foregoing configuration, when the object M is conveyed by conveyor rollers 46c, for example, if it is disabled for some reason to take out the object M from an opening 46b, the unloader 5 is employable to unload the object M, by opening a cover 18. In particular, for an object M with hot temperatures, the unloader 5 implements a useful unloading. For the through holes 47c, a length is determined so that those rays of scattered light incident to gaps between the arms 5a and the through holes 47c are repeatedly reflected therebetween, having sufficiently attenuated intensities. It is noted that sleeves 47d may be provided, as necessary.

Seventh Embodiment

Figure 11:
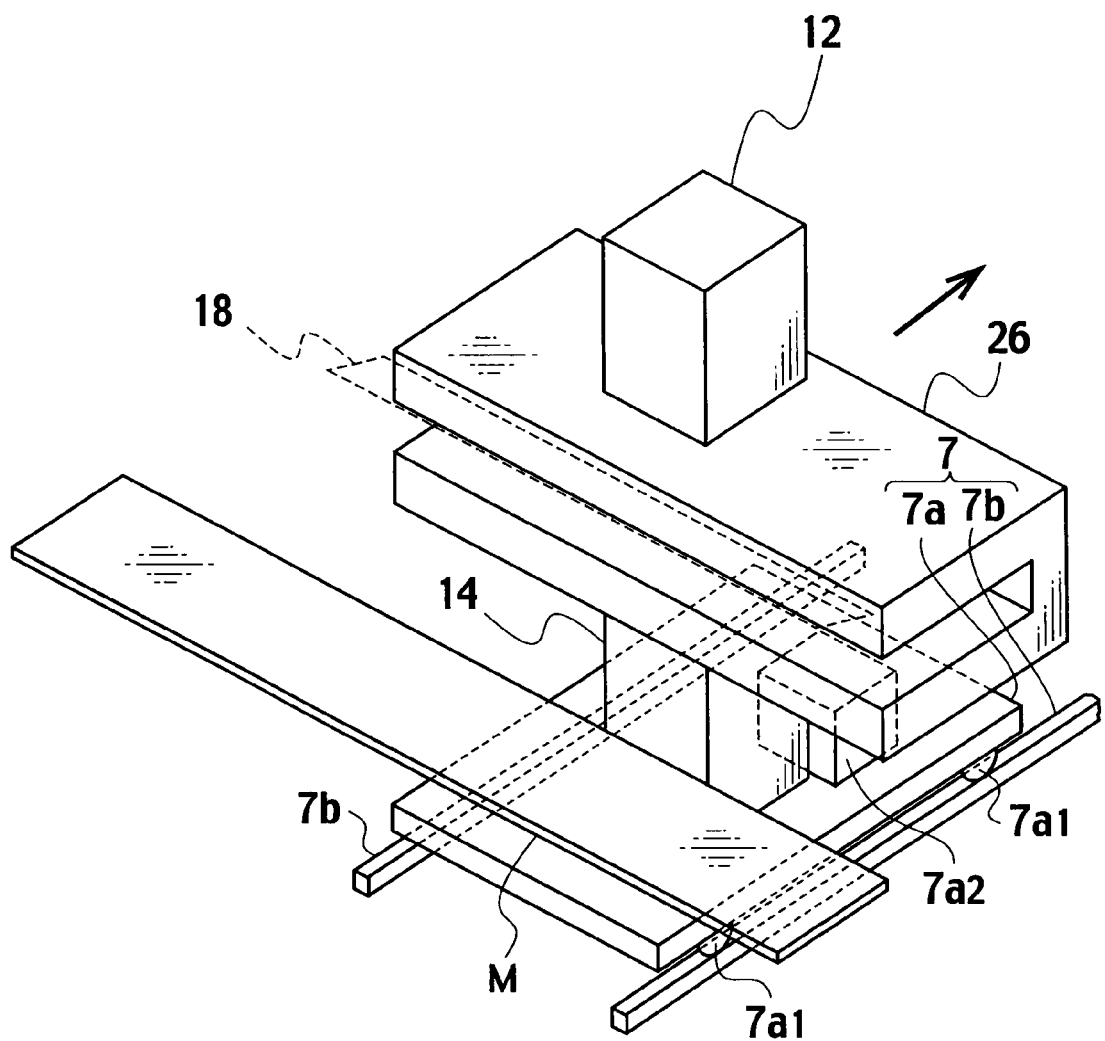
FIG. 11 is a schematic view of a laser ultrasonic property measurement apparatus according to a seventh embodiment of the present invention.

FIG. 11 is a schematic view of a measurement apparatus according to the seventh embodiment of the present invention. As illustrated in the figure, according to the seventh embodiment, a measurement apparatus 60 has a configuration in which a mover 7 is added to the measurement apparatus 20 according to the second embodiment.

The mover 7 includes a truck 7a that is provided with wheels 7a1, and a power source 7a2 for driving wheels 7a1, and has a measurement apparatus 20 mounted thereon, and rails 7b that support the wheels 7a1 to be movable.

According to this configuration, with the power source 7a2 started, the truck 7a moves on the rails 7b, so the measurement apparatus 20 mounted on the truck 7a is moved in the direction of an arrow in FIG. 11. Thus, the seventh embodiment can afford an advantage that it allows maintenance services to be rendered by moving the measurement apparatus 20, for an object M being e.g. long in dimension and difficult to be unloaded.

Eighth Embodiment

Figure 12:
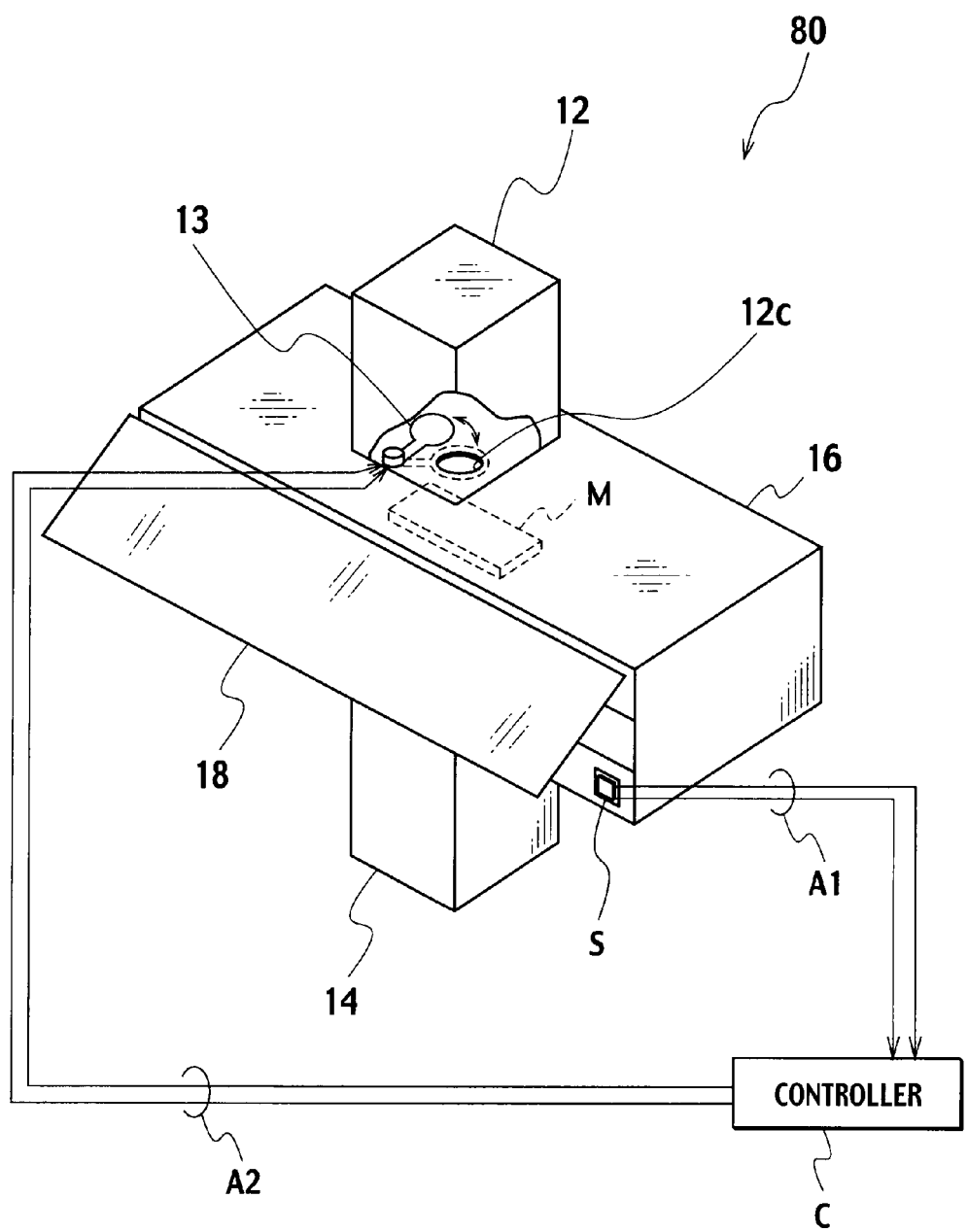
FIG. 12 is a schematic view of a laser ultrasonic property measurement apparatus according to an eighth embodiment of the present invention.
Figure 13:
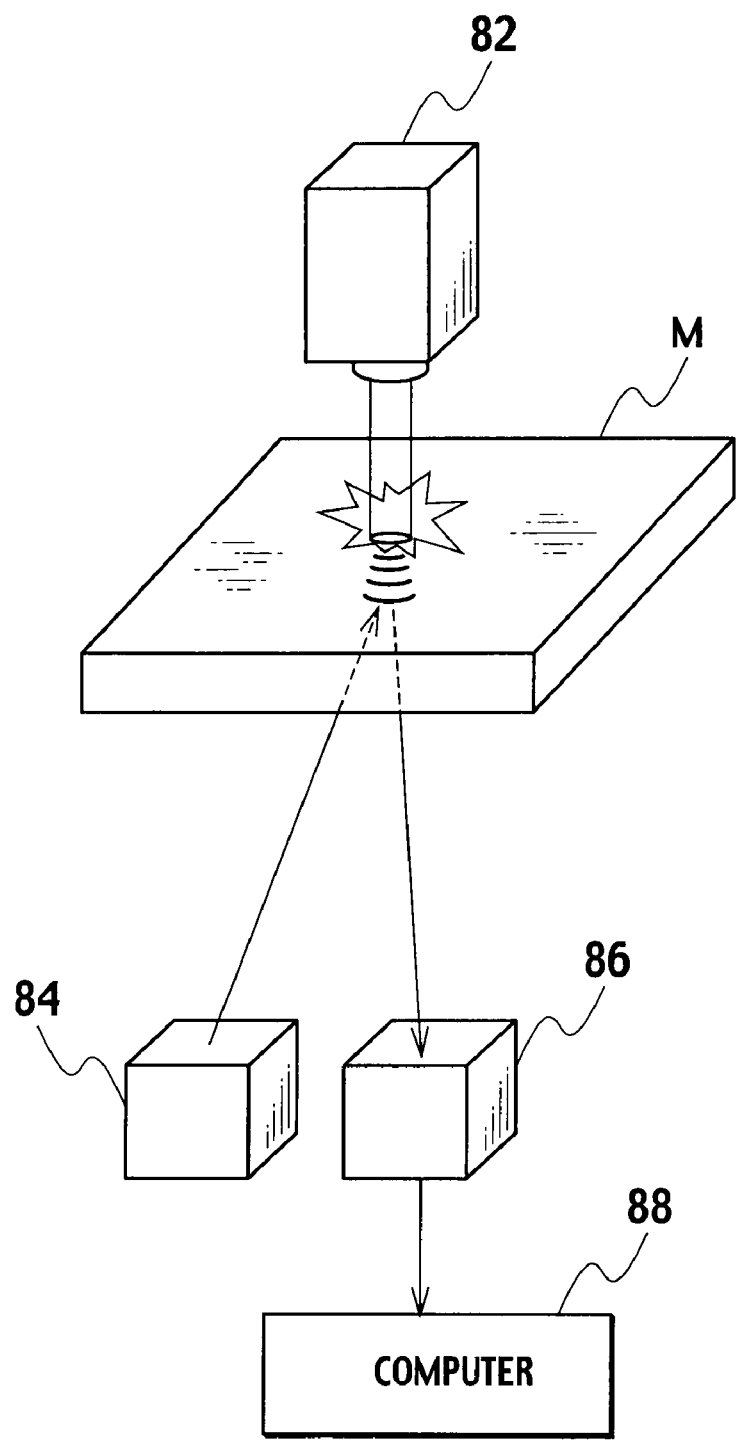
FIG. 13 is a schematic diagram illustrating the principle of a laser ultrasonic property measurement apparatus.

FIG. 12 is a schematic view of a measurement apparatus according to the eighth embodiment of the present invention. As illustrated in the figure, according to the eighth embodiment, a measurement apparatus 80 includes a transmitter 12, a receiver 14, a light blocking structure 16, and a cover 18. The transmitter 12 has a shutter 13 for preventing exciting laser light from a laser light source 12a from being emitted from the transmitter 12. Further, at a lower portion of an opening 16a of the light blocking structure 16, there is a switch S provided for detecting the cover 18 being opened.

When the cover 18 is opened, the switch S as sensing it being opened sends a detection signal to a controller C (arrow A1). The controller C receives the detection signal, and then it sends an instruction signal to the shutter 13 (arrow A2). The shutter 13 as having received the instruction signal rotates, so as to shut a shooting window 12c, thereby preventing exciting laser light from being emitted from the transmitter 12. Further, for the receiver 14 also, there may be provided an open-close operable shutter adapted to prevent emission of laser light, with a configuration for closing the shutter by an instruction signal from the controller C. This is useful in application of high-power probing laser light.

Provision of such an interlock device permits emission of laser light to be cut off, even if the cover 18 is opened in error during measurement, thus allowing for a still ensured safety of workers.

Although there has been described a material measuring apparatus according to the present invention by presenting several embodiments, the present invention is not restricted to those embodiments, and allows a variety of modifications.

Although illustrative description has been made for configurations in which a transmitter 12 and a receiver 14 are arranged outside of a light blocking structure, for example, they may be arranged inside of the light blocking structure for the measurement apparatus 10 in the first embodiment.

It also is possible to additionally provide a deflector for deflecting the direction of travel of exciting laser light emitted from a laser light source 12a of a transmitter 12. By such a configuration, along with a movement of a rolled steel plate of a long size in a light blocking structure 46 or 47, for example, exciting laser light can be deflected in a crossing direction to a direction of the movement, thereby allowing for measurements of crystal grain sizes over a wide range of the rolled steel plate.

Although there has been described a measurement apparatus 50 including a roller 52 and a winder 54 in the fifth embodiment, it may also be useful to implement an interposition of the measurement apparatus 40, such as between a rough roller and a finish roller in a production line of a rolled steel material, or between a finish roller and a winder.

The sixth embodiment has employed hydraulic cylinders 5c, without restriction thereto, providing that the push plate 5b is adapted to push forward an object M.

There has been described a mover 7 including a truck 7a having wheels 7a1 and a power source 7a2, and rails 7b in the seventh embodiment, which however is not restrictive to the mover 7, providing that the measurement apparatus 20 is movable opposite to an opening direction of opening 26a of the light blocking structure 26. For instance, there may be a mover configured with a truck 7a provided with a tractor instead of the power source 7a2, so that the truck 7a is tractable by the tractor. Further, substituting for the provision of a tractor, a truck 7a may be manually moved Although, preferably, the power source 7a2 should be a motor, there may well be a power source using pneumatic pressure, hydraulic pressure, etc. Further, for the seventh embodiment, in which a measurement apparatus is entirely moved, there may be a configuration to simply move the light blocking structure.

INDUSTRIAL APPLICABILITY

According to the present invention, laser light leakage is controlled for a secured safety of workers, which can be implemented not simply for unmanned laboratories, but also for e.g. productions lines of rolled steel plates, permitting a property monitoring during production, allowing for a production of quality steel plates.

The invention claimed is:

1. A laser ultrasonic property measurement apparatus, comprising:
   a transmitter configured to shoot exciting laser light to an object of measurement to excite ultrasonic waves in the object of measurement;
   a receiver configured to shoot probing laser light to the object of measurement to receive reflected light of the probing laser light from the object of measurement for detection of the ultrasonic waves;
   a light blocking structure having a first opening allowing the object of measurement to pass therethrough and adapted to accommodate the object of measurement; and
   a cover adapted to cover and open the first opening, wherein
   the light blocking structure comprises at least one second opening oriented in a perpendicular direction to an opening direction of the first opening, and at least one light blocking plate disposed between the second opening and a location to be irradiated by the exciting laser light.

2. The laser ultrasonic property measurement apparatus according to claim 1, wherein
   a length of the light blocking structure and a first gap distance between the light blocking plate and the object of measurement are determined in dependence on an intensity of scattered light directly leaking from the second opening, a thickness of the object of measurement, and and an amount of warpage of the object of measurement, and
   the location of the light blocking plate is determined in dependence on a ratio between the first gap distance and a second gap distance between the light blocking structure and the object of measurement.

3. The laser ultrasonic property measurement apparatus according to claim 1, further comprising:
   a detector configured to detect the cover being open to the first opening to output a detection signal; and
   a shutter configured to receive the detection signal to prevent the exciting laser light from being emitted.

4. The laser ultrasonic property measurement apparatus according to claim 1, wherein
   the transmitter is configured to be fixed so as to fit in to the light blocking structure.

5. The laser ultrasonic property measurement apparatus according to claim 1, wherein
   the light blocking structure comprises a carrying roller configured to carry the object of measurement.

6. The laser ultrasonic property measurement apparatus according to claim 1, wherein:
   the light blocking structure includes two of said second openings, and
   the laser ultrasonic property apparatus further comprises:
   a feeder arranged to face one of the second openings and configured to feed the object of measurement to the light blocking structure; and
   an acceptor arranged to face the other of the second openings and configured to cooperate with the feeder to provide a tension to the object of measurement being fed from the light blocking structure.

7. The laser ultrasonic property measurement apparatus according to claim 6, wherein
   the feeder is configured to roll the object of measurement in a concurrent function.

8. The laser ultrasonic property measurement apparatus according to claim 6, wherein
   the acceptor includes a winder configured to wind up the object of measurement being fed from the light blocking structure.

9. The laser ultrasonic property measurement apparatus according to claim 1, further comprising:
   an unloader configured to push forward the object of measurement toward the first opening.

10. The laser ultrasonic property measurement apparatus according to claim 1, further comprising:
   a mover configured to move the object of measurement in an opposite direction to an opening direction of the first opening.

* * * * *